(12) United States Patent
An et al.

(10) Patent No.: US 11,832,970 B2
(45) Date of Patent: Dec. 5, 2023

(54) WORSENING HEART FAILURE STRATIFICATION

(71) Applicant: Cardiac Pacemakers, Inc., St. Paul, MN (US)

(72) Inventors: Qi An, Blaine, MN (US); Pramodsingh Hirasingh Thakur, Woodbury, MN (US); Yi Zhang, Plymouth, MN (US); Viktoria A Averina, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 536 days.

(21) Appl. No.: 16/045,862

(22) Filed: Jul. 26, 2018

(65) Prior Publication Data

US 2019/0029601 A1    Jan. 31, 2019

Related U.S. Application Data

(60) Provisional application No. 62/537,110, filed on Jul. 26, 2017.

(51) Int. Cl.
*A61B 5/00* (2006.01)
*A61B 5/02* (2006.01)
*A61B 5/08* (2006.01)
*A61B 5/0205* (2006.01)

(52) U.S. Cl.
CPC .......... *A61B 5/7275* (2013.01); *A61B 5/0205* (2013.01); *A61B 5/02028* (2013.01); *A61B 5/0816* (2013.01); *A61B 5/0826* (2013.01); *A61B 5/0022* (2013.01); *A61B 5/0031* (2013.01); *A61B 5/486* (2013.01); *A61B 5/686* (2013.01); *A61B 5/746* (2013.01)

(58) Field of Classification Search
CPC .... A61B 5/0205; A61B 5/0816; A61B 5/7275
See application file for complete search history.

(56) References Cited

U.S. PATENT DOCUMENTS

| | | | |
|---|---|---|---|
| 7,678,061 B2 | 3/2010 | Lee et al. | |
| 8,372,809 B2 | 2/2013 | Unemori et al. | |
| 8,954,146 B2 | 2/2015 | Hopper et al. | |
| 2006/0195149 A1 | 8/2006 | Hopper et al. | |
| 2007/0073168 A1* | 3/2007 | Zhang | A61N 1/3627 600/483 |

(Continued)

*Primary Examiner* — Carrie R Dorna
*Assistant Examiner* — Karen E Toth
(74) *Attorney, Agent, or Firm* — Schwegman Lundberg & Woessner, P.A.

(57) ABSTRACT

Systems and methods for monitoring patients for risk of worsening heart failure (WHF) are discussed. A patient management system includes a sensor circuit to receive respiration measurements, and an input device to receive patient dyspnea descriptor indicating dyspnea symptom severity. The system includes a risk analyzer circuit to trend the respiration measurement over time, and to generate a WHF risk indicator using both the trended respiration measurement and the received dyspnea descriptor. A control circuit controls the receiver circuit to receive the dyspnea descriptor in response to the trended respiration measurement satisfying a specific condition. The system can present the WHF risk indicator to a user or a process, or deliver or adjust a HF therapy based on the WHF risk indicator.

20 Claims, 6 Drawing Sheets

(56) References Cited

U.S. PATENT DOCUMENTS

| | | | | |
|---|---|---|---|---|
| 2008/0262360 | A1* | 10/2008 | Dalal | A61B 5/0205 |
| | | | | 600/484 |
| 2011/0105860 | A1* | 5/2011 | Houben | G16H 40/63 |
| | | | | 600/301 |
| 2011/0215038 | A1* | 9/2011 | Couturier | E04H 4/16 |
| | | | | 210/167.19 |
| 2011/0275942 | A1* | 11/2011 | Stahmann | G16H 40/67 |
| | | | | 600/483 |
| 2012/0157856 | A1* | 6/2012 | An | A61B 5/0816 |
| | | | | 600/484 |
| 2015/0038854 | A1* | 2/2015 | Zhang | G16H 50/20 |
| | | | | 600/479 |
| 2015/0038866 | A1* | 2/2015 | Zhang | A61B 5/0809 |
| | | | | 600/534 |
| 2015/0250428 | A1* | 9/2015 | Zhang | A61B 5/4842 |
| | | | | 600/301 |
| 2017/0068792 | A1* | 3/2017 | Reiner | A61B 5/0022 |
| 2017/0119317 | A1* | 5/2017 | Thakur | A61B 5/7275 |
| 2017/0281097 | A1* | 10/2017 | Thakur | G16H 50/30 |
| 2017/0311879 | A1* | 11/2017 | Armitstead | A61B 5/0022 |

\* cited by examiner

WORSENING HEART FAILURE STRATIFICATION

CLAIM OF PRIORITY

This application claims the benefit of priority under 35 U.S.C. § 119(e) of U.S. Provisional Patent Application Ser. No. 62/537,110, filed on Jul. 26, 2017, which is herein incorporated by reference in its entirety.

TECHNICAL FIELD

This document relates generally to medical devices, and more particularly, to systems, devices and methods for assessing patient risk of worsening heart failure.

BACKGROUND

Congestive heart failure (CHF) is a leading cause of death in the United States and globally. CHF is the loss of pumping power of the heart, resulting in the inability to deliver enough blood to meet the demands of peripheral tissues. CHF patients typically have enlarged heart with weakened cardiac muscles, resulting in reduced contractility and poor cardiac output of blood. CHF may be treated by drug therapy, or by an implantable medical device (IMD) such as for providing electrostimulation therapy. CHF is usually a chronic condition, but can occur suddenly. It can affect the left heart, right heart or both sides of the heart.

Dyspnea, generally refers to a sensation of shortness of breath or difficult breathing, is a common symptom of CHF. Dyspnea may be caused by heart or lung disorders, strenuous activity, high anxiety or stress. Dyspnea derives from interactions among multiple physiological, psychological, social, and environmental factors, and may induce secondary physiological and behavioral responses. Dyspnea may be classified as chronic, acute, or terminal. Chronic dyspnea has a variable intensity and persistent shortness of breath. This is most often seen in patients with chronic obstructive pulmonary disease (COPD). Acute dyspnea causes episodes of shortness of breath with high intensity. It may be seen in patients who have suffered a myocardial infarction or pulmonary embolism. Terminal dyspnea occurs in patients with end-stage diseases, and these patients may be in a hospital, at home, or in a hospice. This type of dyspnea is a common complaint in patients with cancer. Dyspnea can be caused by a variety of conditions, including metabolic, allergic, psychiatric, and neuromuscular disorders, and by pain. However, cardiac and pulmonary disorders are the most common causes.

Some IMDs can monitor CHF patients and detect events leading to worsening heart failure (WHF). These IMDs may include sensors to sense physiological signals from a patient. Frequent patient monitoring may help reduce heart failure hospitalization. Identification of patient at an elevated risk of developing WHF, such as heart failure decompensation, may help ensure timely treatment and improve prognosis and patient outcome. Identifying and safely managing the patients at elevated risk of WHF can avoid unnecessary medical interventions, hospitalization, and thereby reduce healthcare cost.

Some IMDs contain electronic circuitry, such as a pulse generator, that can generate and deliver electrostimulation to excitable tissues or organs, such as a heart. The electrostimulation may help restore or improve a CHF patient's cardiac performance, or rectify cardiac arrhythmias. One example of such electrostimulation therapy is resynchronization therapy (CRT) for correcting cardiac dyssynchrony in CHF patients.

SUMMARY

CHF patients frequently present with dyspnea with exertion, orthopnea (a sensation of breathlessness in a recumbent position), or paroxysmal nocturnal dyspnea (a sensation of shortness of breath that awakens the patient). Dyspnea may occur initially upon exertion, but in advanced CHF it may occur at rest, or when lying down. In diastolic heart failure, increased pressure can build up in the heart during the period of relaxation, or diastole.

Dyspnea in CHF may be related to abnormal pulmonary fluid accumulation. In CHF patient, low cardiac pump efficiency may cause the blood to back up into the veins that take blood through the lungs. As the pressure in these blood vessels increases, fluid is pushed into the air spaces (alveoli) in the lungs. Fluid accumulation in the lungs may lead to pulmonary edema and elevated ventricular filling pressure. The fluid buildup also reduces normal oxygen movement through the lungs. These two factors combine to cause dyspnea.

Dyspnea may have causes other than CHF. For example, acute dyspnea or respiratory distress may be caused by asthma, cardiac tamponade, hypotension, pulmonary embolism, pneumonia, or upper airway obstruction, among others. Chronic dyspnea can also indicate chronic conditions other than CHF, such as asthma, COPD, deconditioning, or non-cardiac or non-pulmonary causes such as metabolic conditions, pain, neuromuscular disorders, panic disorders and anxiety, or hyperventilation, among others. As such, although dyspnea symptom is a useful diagnostic of WHF, it can be non-specific in some patients. As a subjective measure, dyspnea symptom can be affected by patient perceptual, cognitive, and communicative abilities. This can result in substantial inter-patient variability, or intra-patient variability in some patients. Additionally, dyspnea symptoms are usually obtained through patient interrogation conducted by a clinician in a clinic visit. Information about dyspnea symptom may not be timely acquired due to the constraints in time and location of patient interrogation.

Pulmonary fluid accumulation in CHF patient may cause respiratory changes including changes in respiratory rate, depth, timing, regularity, or respiratory pattern. Respiration monitoring, such as using an AMD, provide diagnostic of WHF status. Patients with respiratory changes, such as elevated respiratory rate or a change in respiratory pattern, may have a higher WHF risk. Respiratory changes, however, may not be very specific to WHF. Some patients having diseases other than WHF, such as chronic respiratory disease, may present with similar respiratory changes. For example, asthma and chronic obstructive pulmonary disease (COPD) are common chronic respiratory conditions, and may coexist in some patients. Patients with asthma or COPD can present symptoms including chronic coughing, wheezing, shortness of breath, or hyper-responsiveness to airflow during inspiration, among others. Particularly in an ambulatory setting, respiration measurements may be susceptible to physiological or environmental interferences or be contaminated by noise. The confounding diseases or conditions, or the noise and interferences, may adversely affect the accuracy and reliability of WHF event detection or WHF risk stratification.

The present inventors have recognized a challenge in HF monitoring, namely an accurate and reliable identification of patients at elevated risks of WHF. The present inventors have also recognized that, in addition to the objective diagnostic of sensor-indicated respiratory changes, subjective diagnostic such as patient symptomatic dyspnea may provide additional benefit that complements the predictive power of the sensor-indicated respiratory changes. In a computerized system, a combination of dyspnea symptom information with sensor-based respiration measurements may outperform an individual diagnostic, and may improve sensitivity, specificity, and predictive value of WHF event detection or WHF risk stratification. As a result, better patient management can be achieved and the healthcare cost can be reduced.

This document discusses, among other things, a patient management system for assessing patient risk of WHF. The system may receive a respiration measurement such as a respiratory rate, timing, depth, regularity, or respiratory pattern, and a dyspnea descriptor indicating a presence or absence of, or severity of, dyspnea symptom of the patient. A risk analyzer circuit may generate a WHF risk indicator. A control circuit can trend the respiration measurement over time, and control the risk analyzer circuit to generate a WHF risk indicator using both the trended respiration measurement and the received dyspnea descriptor. The system may include an optional therapy circuit to deliver or adjust a HF therapy based on the WHF risk indicator.

Example 1 is a system for identifying a worsening heart failure (WHF) risk of a patient. The system comprises a receiver circuit and a risk analyzer circuit. The receiver circuit may receive a respiration measurement and a dyspnea descriptor indicating a dyspnea symptom severity of the patient. The risk analyzer circuit may trend the respiration measurement over time, and generate a WHF risk indicator using both the trended respiration measurement and the received dyspnea descriptor.

In Example 2, the subject matter of Example 1 optionally includes a control circuit that may control the receiver circuit to receive the dyspnea descriptor in response to the trended respiration measurement satisfying a specific condition.

In Example 3, the subject matter of Example 2 optionally includes the control circuit that may control the receiver circuit to receive the dyspnea descriptor periodically at a specific time.

In Example 4, the subject matter of any one or more of Examples 1-2 optionally includes the risk analyzer circuit that may trend the respiration measurement over time in response to the received dyspnea descriptor satisfying a specified condition.

In Example 5, the subject matter of any one or more of Examples 1-4 optionally includes the receiver circuit that may be coupled to a respiration sensor circuit. The respiration sensor circuit may sense, from the patient, a respiratory signal and to acquire the respiration measurement from the sensed respiratory signal.

In Example 6, the subject matter of any one or more of Examples 1-5 optionally includes the respiration measurement that may include a respiratory rate or a respiratory rate variability.

In Example 7, the subject matter of any one or more of Examples 1-6 optionally includes the respiration measurement that may include a rapid-shallow breathing index (RSBI) or a RSBI variability.

In Example 8, the subject matter of any one or more of Examples 1-7 optionally includes the receiver circuit that may be coupled to an external device. The external device may receive a user input of the dyspnea descriptor.

In Example 9, the subject matter of Example 8 optionally includes the external device that may include a mobile device communicatively coupled to the risk analyzer circuit.

In Example 10, the subject matter of any one or more of Examples 8-9 optionally includes the external device that may receive a user command to trend the respiration measurement over time and to activate the risk analyzer circuit to generate the WHF risk indicator.

In Example 11, the subject matter of any one or more of Examples 1-10 optionally includes the dyspnea descriptor that may include a rating of dyspnea symptom severity on a specific rating scale.

In Example 12, the subject matter of Example 11 optionally includes the risk analyzer circuit that may generate the WHF risk indicator using a combination of the rating of dyspnea symptom severity and the trended respiration measurement each weighted by respective weight factors.

In Example 13, the subject matter of any one or more of Examples 1-12 optionally includes the risk analyzer circuit that may generate the WHF risk indicator including one of: a high WHF risk if the trended respiration measurement exceeds a respiration threshold and the received dyspnea descriptor indicates a presence of dyspnea; a medium WHF risk if (1) the trended respiration measurement exceeds the respiration threshold without a presence of dyspnea, or (2) the trended respiration measurement falls below the respiration threshold and the received dyspnea descriptor indicates a presence of dyspnea; or a low WHF risk if the trended respiration measurement falls below the respiration threshold and the received dyspnea descriptor indicates an absence of dyspnea.

In Example 14, the subject matter of any one or more of Examples 1-13 optionally includes an ambulatory medical device that may include one or more of the receiver circuit or the risk analyzer circuit.

In Example 15, the subject matter of any one or more of Examples 1-14 optionally includes an output circuit configured to generate an alert of the WHF risk indicator.

Example 16 is a method for identifying a worsening heart failure (WHF) risk of a patient via a medical system. The method comprises steps of: receiving a respiration measurement via a receiver circuit; receiving a dyspnea descriptor via the receiver circuit, the dyspnea descriptor indicating a dyspnea symptom severity of the patient; trending the respiration measurement over time via a risk analyzer circuit; and generating, via the risk analyzer circuit, a WHF risk indicator using both the trended respiration measurement and the received dyspnea descriptor.

In Example 17, the subject matter of Example 16 optionally includes receiving the dyspnea descriptor in response to the trended respiration measurement satisfying a specific condition.

In Example 18, the subject matter of Example 17 optionally includes generating a prompt on an external device for a user input of the dyspnea descriptor in response to the trended respiration measurement satisfying the specific condition.

In Example 19, the subject matter of Example 16 optionally includes trending the respiration measurement in response to the received dyspnea descriptor satisfying a specified condition.

In Example 20, the subject matter of Example 16 optionally includes the respiration measurement that may include at least one of: a respiratory rate; a respiratory rate variability; a rapid-shallow breathing index (RSBI); or a RSBI variability.

In Example 21, the subject matter of Example 16 optionally includes generating the WHF risk indicator. The WHF risk indicator may include one of: a high WHF risk if the trended respiration measurement exceeds a respiration threshold and the received dyspnea descriptor indicates a presence of dyspnea; a medium WHF risk if (1) the trended respiration measurement exceeds the respiration threshold without a presence of dyspnea, or (2) the trended respiration measurement falls below the respiration threshold and the received dyspnea descriptor indicates a presence of dyspnea; or a low WHF risk if the trended respiration measurement falls below the respiration threshold and the received dyspnea descriptor indicates an absence of dyspnea.

In Example 22, the subject matter of Example 16 optionally includes the dyspnea descriptor that may include a rating of dyspnea symptom severity on a specific rating scale, and generating the WHF risk indicator using a combination of the rating of dyspnea symptom severity and the trended respiration measurement each weighted by respective weight factors.

Various embodiments described herein can help improve the medical technology of device-based heart failure patient management, particularly computerized detection of progression of a chronic disease such as worsening HF, and automated identification of patients at elevated WHF risk. As discussed above, conventional sensor-based detection of respiratory changes for WHF detection may be less specific to WHF and susceptible to interferences. Dyspnea symptom may present in a number of cardiac, pulmonary, neurological, or psychological disorders. In addition to false positives, description of dyspnea symptoms are subjective and may not be readily available. The present inventors have recognized that the information about patient symptomatic dyspnea has a predictive power complementary to that of respiratory rate or other respiratory parameters, and can therefore enhance the accuracy and reliability of identifying patient WHF risk. Systems, devices, and methods that combine the subjective dyspnea symptom with the objective sensor-based respiration measurements, as discussion this document, therefore provide technological solutions to the challenge in computerized WHF assessment.

With the improved WHF risk assessment, the systems and methods discussed herein may timely and reliably identify patients at WHF risk at little to no additional cost. Such improvement in HF patient management can reduce hospitalization and healthcare costs associated with patient management. The systems, devices, and methods discussed in this document may also allow for more efficient device memory usage, such as by storing WHF risk indicators that are clinically more relevant to WHF diagnosis and risk stratification. As fewer false positive detections of WHF events are provided, device battery life can be extended; fewer unnecessary drugs and procedures may be scheduled, prescribed, or provided. Therapy titration, such as electrostimulation parameter adjustment, based on the generated WHF risk, may not only improve therapy efficacy and patient outcome, but may also save device power. As such, overall system cost savings may be realized.

Although the discussion in this document focuses WHF risk assessment, this is meant only by way of example and not limitation. It is within the contemplation of the inventors, and within the scope of this document, that the systems, devices, and methods discussed herein may also be used to detect, and alert occurrence of, cardiac arrhythmias, syncope, respiratory disease, or renal dysfunctions, among other medical conditions. Additionally, although systems and methods are described as being operated or exercised by clinicians, the entire discussion herein applies equally to organizations, including hospitals, clinics, and laboratories, and other individuals or interests, such as researchers, scientists, universities, and governmental agencies, seeking access to the patient data.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for monitoring a patient for WHF. A patient management system may include a sensor circuit to receive respiration measurements such as respiratory rate, depth, timing, regularity, or respiratory pattern. The system may receive patient dyspnea descriptor indicating a presence or absence of, or severity of, dyspnea symptom. The system may trend the respiration measurement over time, and control a risk analyzer circuit to generate a WHF risk indicator using both the trended respiration measurement and the received dyspnea descriptor. The WHF risk indicator may be presented to a system user or a process. A therapy circuit may deliver or adjust a HF therapy based on the WHF risk indicator.

Figure 1:
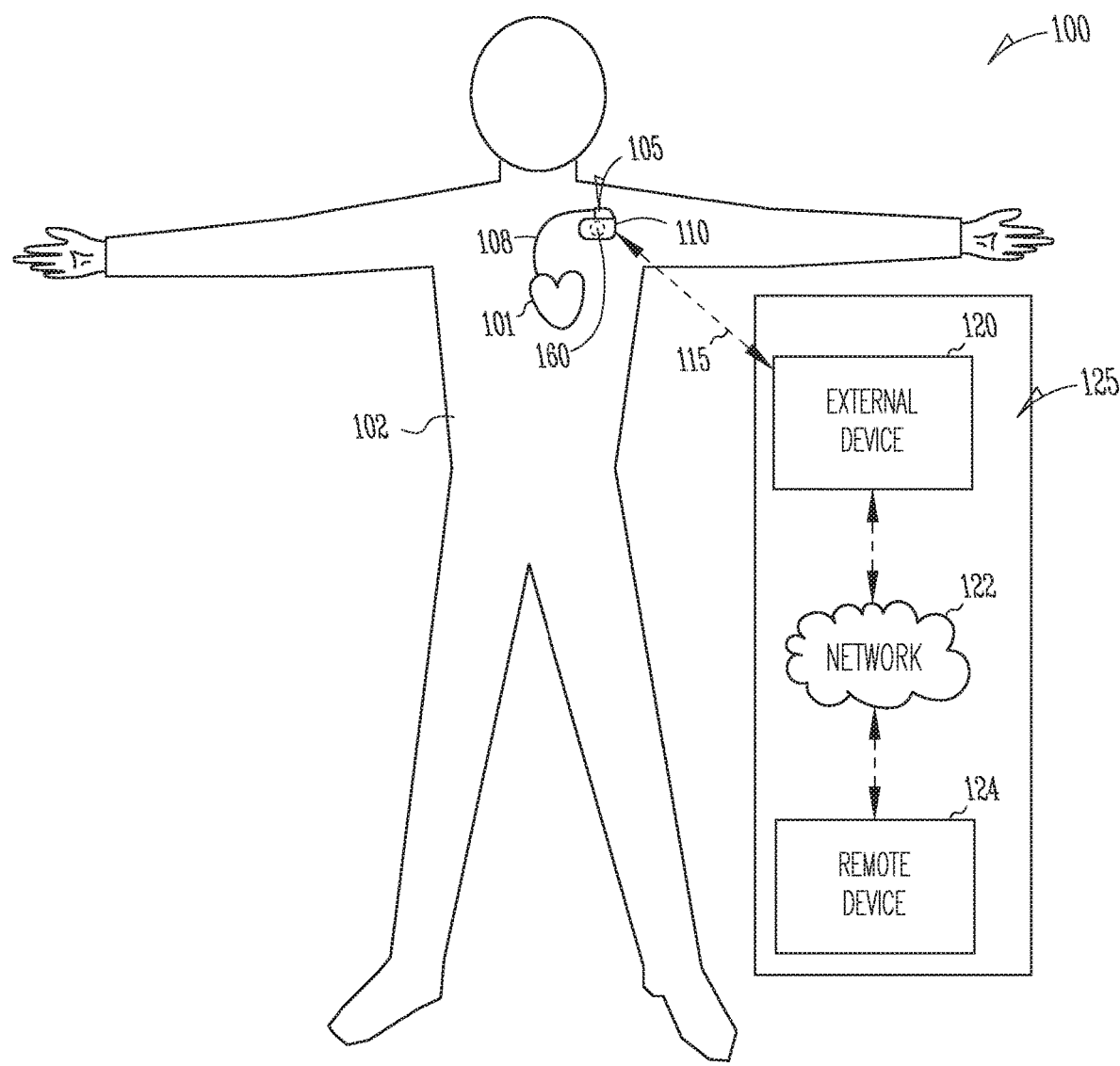
FIG. 1 illustrates generally an example of a patient monitor system and portions of an environment in which the system may operate.

FIG. 1 illustrates generally an example of a patient monitor system 100 and portions of an environment in which the system 100 may operate. The patient monitor system 100 may chronically monitor a patient 102 to assess patient risk of developing WHF. Portions of the system 100 may be ambulatory. Portions of the system 100 may be disposed in a patient home or office, a hospital, a clinic, or a physician's office.

As illustrated in FIG. 1, the patient monitor system 100 may include an ambulatory system 105 associated with the patient 102, an external system 125, and a telemetry link 115 providing for communication between the ambulatory system 105 and the external system 125. The ambulatory syssystem 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart wearables, or smart accessories.

By way of example and not limitation, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiological signal indicative of cardiac activity, or physiological responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiological signal containing information about patient heart rate or pulse rate. In an example, the ambulatory system 105 may include one or more leadless sensors not being tethered to the AMD 110 via the lead system 108. The leadless ambulatory sensors may be configured to sense a physiological signal and wirelessly communicate with the AMD 110.

The AMD 110 may include a hermetically sealed can that houses one or more of a sensing circuit, a control circuit, a communication circuit, and a battery, among other components. The sensing circuit may sense a physiological signal, such as by using a physiological sensor or the electrodes associated with the lead system 108. The physiological signals may contain information about patient physiological response to a precipitating event associated with onset of a future WHF event. The physiological signal may represent changes in patient hemodynamic status. Examples of the physiological signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiological response to activity, posture, respiratory rate, tidal volume, respiratory sounds, body weight, or body temperature.

The AMD 110 may include a risk assessment circuit 160 configured to assess a patient risk of developing a worsened chronic disease or condition, such as WHF. The risk assessment circuit 160 may include a sensor circuit to receive respiration measurements such as respiratory rate, depth, timing, regularity, or respiratory pattern. The risk assessment circuit 160 may be communicatively coupled to an input device, such as a mobile device, configured to receive a dyspnea descriptor indicating a presence or absence, or severity of dyspnea symptom. The risk assessment circuit 160 may trend the respiration measurements over time, and generate a WHF risk indicator using both the trended respiration measurement and the dyspnea descriptor. The WHF risk indicator indicates a likelihood of the patient's risk of developing a future WHF event, such as a HF decompensation event. Examples of the HF event detection/risk assessment are described below, such as with reference to FIGS. 2-4. In various examples, the risk assessment circuit 160 may be configured to detect worsening of other diseases or conditions including, for example, cardiac arrhythmias, syncope, respiratory disease such as COPE or asthma, or renal dysfunctions, among other medical conditions.

The AMD 110 may include a therapy unit that may generate and deliver a therapy to the patient. The therapy may be preventive (e.g., to prevent development into a full-blown), or therapeutic (e.g., to treat heart failure or alleviate complications) in nature, and may modify, restore, or improve patient physiological functionalities. Examples of the therapy may include electrical, magnetic, or other forms of therapy. In some examples, the AMD 110 may include a drug delivery system such as a drug infusion pump device to deliver drug therapy to the patient. In some examples, the AMD 110 may monitor patient physiological responses to the delivered to assess the efficacy of the therapy.

The external system 125 may include a dedicated hardware/software system such as a programmer, a remote server-based patient management system, or alternatively a system defined predominantly by software running on a standard personal computer. The external system 125 may manage the patient 102 through the AMD 110 connected to the external system 125 via a communication link 115. This may include, for example, programming the AMD 110 to perform one or more of acquiring physiological data, performing at least one self-diagnostic test (such as for a device operational status), analyzing the physiological data to generate a WHF risk indicator, or optionally delivering or adjusting a therapy to the patient 102. The external system 125 may communicate with the AMD 110 via the communication link 115. The device data received by the external system 125 may include real-time or stored physiological data from the patient 102, diagnostic data, responses to therapies delivered to the patient 102, or device operational status of the AMD 110 (e.g., battery status and lead impedance). The communication link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device. The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

The remote device 124 may include a centralized server acting as a central hub for collected patient data storage and analysis. The patient data may include data collected by the AMD 110, and other data acquisition sensors or devices associated with the patient 102. The server may be configured as a uni-, multi- or distributed computing and processing system. In an example, the remote device 124 may include a data processor configured to perform HF detection or risk stratification using respiration data received by the AMD 110 and information about patient dyspnea symptom received from an input device such as a mobile device. Computationally intensive algorithms, such as machine-learning algorithms, may be implemented in the remote device 124 to process the data retrospectively to detect WHF or analyze patient WHF risk. The remote device 124 may generate an alert notification. The alert notifications may include a Web page update, phone or pager call, E-mail, SMS, text or "Instant" message, as well as a message to the patient and a simultaneous direct notification to emergency services and to the clinician. Other alert notifications are possible.

One or more of the external device 120 or the remote device 124 may output the WHF detection or the WHF risk to a system user such as the patient or a clinician. The external device 120 or the remote device 124 may include respective display for displaying the physiological data acquired by the AMD 110. The physiological data may be presented in a table, a chart, a diagram, or any other types of textual, tabular, or graphical presentation formats. The external device 120 or the remote device 124 may include a printer for printing hard copies of signals and information related to the generation of WHF risk indicator. The presentation of the output information may include audio or other media format. In an example, the output unit 254 may generate alerts, alarms, emergency calls, or other forms of warnings to signal the system user about the WHF detection or risk. The clinician may review, perform further analysis, or adjudicate the WHF detection or WHF risk. The WHF detection or the WHF risk, optionally along with the data acquired by the AMD 110 and other data acquisition sensors or devices, may be output to a process such as an instance of a computer program executable in a microprocessor. In an example, the process may include an automated generation of recommendations for initiating or adjusting a therapy, or a recommendation for further diagnostic test or treatment.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
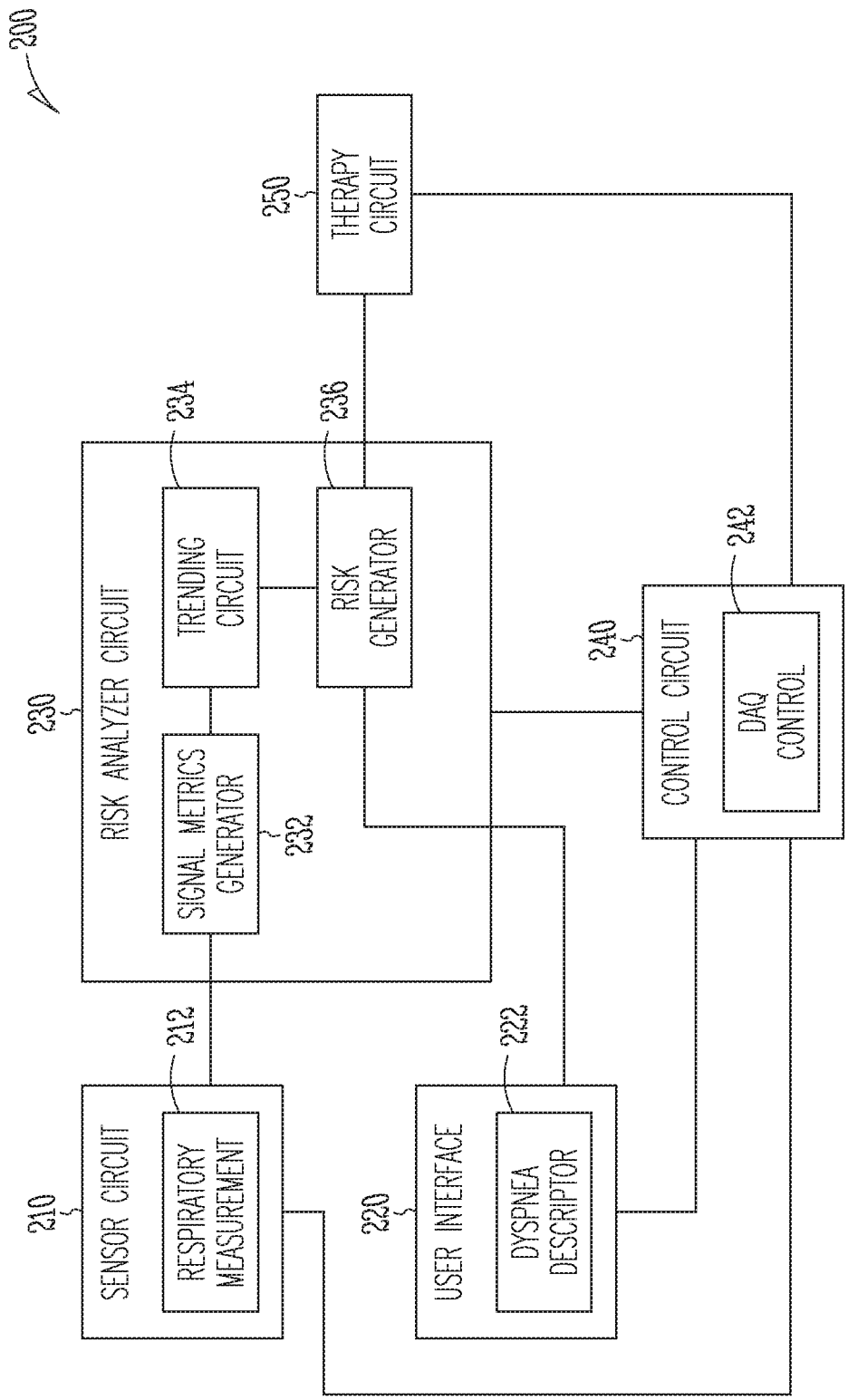
FIG. 2 illustrates generally an example of a HF monitor system configured to assess a risk of WHF of a patient.

FIG. 2 illustrates generally an example of a HF monitor system 200 that may be configured to assess a risk of WHF of a patient. At least a portion of the HF monitor system 200 may be implemented in the AMD 110, the external system 125 such as one or more of the external device 120 or the remote device 124, or distributed between the AMD 110 and the external system 125. The HF monitor system 200 may include one or more of a sensor circuit 210, a user interface 220, a risk analyzer circuit 230, and a control circuit 240. The HF monitor system 200 may include an optional therapy circuit 250 for delivering a HF therapy.

The sensor circuit 210 may include a sense amplifier circuit to sense at least one physiological signal from a patient. The sensor circuit 210 may be coupled to an implantable, wearable, or otherwise ambulatory sensor or electrodes associated with the patient. The sensor may be incorporated into, or otherwise associated with an ambulatory device such as the AMD 110. Examples of the physiological signals for detecting the precipitating event may include surface electrocardiography (ECG) sensed from electrodes placed on the body surface, subcutaneous ECG sensed from electrodes placed under the skin, intracardiac electrogram (EGM) sensed from the one or more electrodes on the lead system 108, heart rate signal, physical activity signal, or posture signal, a thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal, physiological response to activity, apnea hypopnea index, one or more respiration signals such as a respiratory rate signal or a tidal volume signal, brain natriuretic peptide (BNP), blood panel, sodium and potassium levels, glucose level and other biomarkers and bio-chemical markers, among others. In some examples, the physiological signals sensed from a patient may be stored in a storage device, such as an electronic medical record (EMR) system, and the sensor circuit 210 may be configured to receive a physiological signal from the storage device in response to a user input or triggered by a specific event.

The sensor circuit 210 may be coupled to an implantable, wearable, holdable, or other ambulatory respiratory sensor configured to acquire a respiration measurement 212. Various respiratory sensors may be used to measure directly or indirectly a change in airflow or a change in lung volume during respiratory cycles. In an example, a flowmeter may be configured to sense directly the airflow in the respiratory system or volume change in the lungs. In another example, the respiratory sensor may be coupled to electrodes attached to or implanted in the patient to sense the respiration signal from the patient. Some respiratory sensors may sense a physiological signal modulated by respiration. In an example, the thoracic impedance may vary at different respiratory phases, such that the impedance increases during inspiration and decreases during expiration. The thoracic impedance may be measured using electrodes on an implantable lead coupled to an implantable medical device. In an example, thoracic impedance may be measured between an electrode on a right ventricular and the can housing of the implantable device implanted at a pectoral region, between an electrode on a left ventricle and the can housing of the implantable device, or between a right atrium electrode and the can housing of the implantable device. The thoracic impedance may alternatively be measured using non-invasive surface electrodes removably attached to a patient chest.

In various examples, respiration may be sensed using one or more of a strain sensor configured to sense changes in chest muscle tension corresponding to respiration cycles, an accelerometer to measure acceleration associated with displacement or movement of check walls corresponding to respiration, or an acoustic sensor to sense cardiac acoustic signal that is modulated by respiration. In an example, respiration signal may be extracted from a cardiac electrical signal, such as an electrocardiograph (ECG). ECG signal may be modulated by respiration signal. During inspiration, the diaphragm shift downwards away from the apex of the heart. The increased filling of the lungs further stretch the apex of the heart towards the abdomen. During expiration, the lung volume reduces, and the diaphragm elevates upwards toward the heart, which compresses the apex of the heart towards the breast. As a result, the angle of the electric cardiac vector that gives rise to the ECG signal changes during inspiration and respiratory phases, which leads to cyclic variation in R-wave amplitude on the ECG signal. The respiration signal can be obtained from the R-wave amplitude signal using demodulation method, such as by filtering an R-wave amplitude trend through a low-pass filter or a bandpass filter. Other respiratory sensors may alternatively include patient-external respiratory bands, respiration flowmeter, implantable or patient-external breath sound detector, blood oxygen detector, and other sensors configured to sense a respiration-modulated physiological signal, which can be found in Lee et al., U.S. Pat. No. 7,678,061 entitled "System and method for characterizing patient respiration", filed on Apr. 15, 2004, which is incorporated herein by reference in its entirety.

The sensor circuit 210 may include one or more sub-circuits to digitize, filter, or perform other signal conditioning operations on the sensed physiological signal. The sensor circuit 210 may detect from the sensed respiration signal a plurality of respiratory cycles, and determine for each respiratory cycle a respiratory cycle period, or a respiratory rate. The sensor circuit 210 may detect, within each respiratory cycle, an inspiration phase and an expiration phase. The inspiration phase is a period between an end-of-expiration state and the next end-of-inspiration state. The expiration phase is a period between an end-of-inspiration state and the next end-of-expiration state. In an example where the respiratory sensor directly or indirectly measures the lung volume, the end-of-expiration state may correspond to the minimal lung volume within a specified detection window; and the end-of-inspiration state may correspond to the maximal lung volume with a specified detection window. In another example where the respiratory sensor senses thoracic impedance, the thoracic impedance increases when the air volume in the lungs increases. The end-of-expiration state may correspond to the minimal transthoracic impedance within a specified detection window; and the end-of-inspiration state may correspond to the maximal transthoracic impedance within a specified detection window.

The user interface 220, which may be implemented in the external system 125, includes an input circuit that may receive a user input of a dyspnea descriptor 222. The dyspnea descriptor 222 characterizes the presence or absence, or severity of patient perception of shortness of breath, and may take different forms. In an example, the dyspnea descriptor 222 may include verbal or written (e.g., textual or graphical) description of patient dyspnea symptom. In another example, the dyspnea descriptor 222 may take categorical values of dyspnea severity, such as one or more of "no dyspnea", "mild dyspnea", "moderate dyspnea", or "severe dyspnea", among other categorical values. In another example, the dyspnea descriptor 222 may take categorical values of dyspnea types, such as one or more of "no dyspnea", "dyspnea on exertion", or "dyspnea at rest", among others. In another example, the dyspnea descriptor 222 may take binary values of "Yes" or "No" to different types of dyspnea, such as one or more of "dyspnea on exertion", "dyspnea at rest", "orthopnea", or "paroxysmal nocturnal dyspnea", among others. In an example, the dyspnea descriptor 222 may take numerical values such as according to a rating scale from zero to ten. The rating scale corresponds to elevated degrees of dyspnea intensity. A dyspnea score of zero indicates no respiratory distress or shortness of breath. A dyspnea score of ten indicates intolerable and an extreme severity of symptomatic dyspnea. The categorical dyspnea values may correspond to characteristic verbal or written symptom descriptions. For example, mild dyspnea may be associated with descriptive terms and phrases such as "a little out of breath", "some difficulty breathing during activity", "slightly anxious". Moderate dyspnea may be associated with terms or phrases such as "can't catch my breath", "can't go upstairs without stopping", "it takes longer to get to the mailbox", "can't lay flat", "sleep on a chair", "pop up with a couple of pillows at night", "wheezing or hacking sound while coughing or breathing", "shallow or pursed lip breathing", or "anxious or shaky". Severe dyspnea may be associated with descriptive language such as "severe shortness of breath at rest", "rapid, shallow or pursed lip breathing", or "very anxious or panicky." The categorical dyspnea values may also correspond to a range of numerical dyspnea scores. For example, dyspnea scores 1-3 are "mild" dyspnea, dyspnea scores 4-6 are "moderate" dyspnea, and dyspnea scores 7-10 correspond to "severe" dyspnea.

The user interface 220 may include a display to display a questionnaire or a rating scale, and prompt a user to enter information about dyspnea sensation, such as intensity, duration, pattern, or other dyspnea symptom descriptors. A user, such as the patient or a healthcare professional, may use a keyboard, an on-screen keyboard, a mouse, a trackball, a touchpad, a touch-screen, or other pointing or navigating devices to enter information about patient dyspnea symptom. In some examples, a user may be prompted to make selections from a plurality of pre-determined dyspnea descriptors. In addition to receiving user input about dyspnea symptom, the user interface 220 may receive other user input for programming one or more system components, such as the sensor circuit 210, the risk analyzer circuit 230, or the therapy circuit 250.

The risk analyzer circuit 230 may generate a WHF risk indicator using the respiration measurement 212 and the received dyspnea descriptor 222. The risk analyzer circuit 230 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The risk analyzer circuit 230 may include circuit sets comprising one or more other circuits or sub-circuits including a signal metrics generator 232, a trending circuit 234, and a risk generator 236. These circuits or sub-circuits may, either individually or in combination, perform the functions, methods or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The signal metrics generator 232 may generate one or more metrics from the respiration measurement. Examples of the respiratory metrics may include a respiratory rate, a tidal volume, a minute ventilation, a respiratory sound, a rapid-shallow breathing index (RSBI) computed as a ratio of a respiratory rate measurement to a tidal volume measurement, or a respiratory pattern (e.g., Cheyne-Stokes pattern, cluster breathing, Kussmaul's breathing, apneustic breathing, or ataxic breathing), among other respiratory metrics. Statistical measures, such as mean, median, variance, standard deviation, range, or other first order, second order, or higher order statistics of one or more of the respiratory parameters may be generated. The trending circuit 234 may trend the one or more respiratory metrics over time. In an example, the trending circuit 234 may generate one or more of a respiratory rate trend (RRT), a RSBI trend, a respiratory rate variability trend, or a RSBI variability trend.

The risk generator 236, coupled to the trending circuit 234 and the user interface 220, may be configured to generate a WHF risk indicator using both the respiratory parameter trend and the dyspnea descriptor. The present inventors have recognized that the information about patient symptomatic dyspnea has a predictive power complementary to that of the respiratory change. Incorporating the subjective diagnostic of dyspnea symptom into the sensor-based HF monitor may enhance the accuracy and reliability of identifying patient WHF risk. Examples of the statistical analysis of WHF risk in patients having one or both of dyspnea symptom and respiratory changes are discussed below, such as with reference to FIG. 4.

The risk generator 236 may determine the WHF risk indicator using a computation model that performs linear nonlinear combination of the respiratory parameter trend and the dyspnea descriptor. Examples of the computation models may include a weighted combination, a decision tree, a neural network, a fuzzy-logic model, or a multivariate regression model, among others. In an example, the risk generator 236 may determine the WHF risk indicator using a logic combination of the respiratory parameter trend and the dyspnea descriptor. For example, the risk generator 236 may determine that a patient has a high WHF risk if the respiratory parameter trend exceeds a respiration threshold and the dyspnea descriptor indicates the patient has symptomatic dyspnea. A medium WHF risk may be determined if the respiratory parameter trend exceeds the respiration threshold but the patient if free of dyspnea symptom, or if the patient has symptomatic dyspnea but the respiratory parameter trend falls below the threshold. The risk generator 236 may determine that the patient has a low WHF risk if the respiratory parameter trend falls below the respiration threshold, and the patient has no symptom of dyspnea.

In some examples, two or more respiratory parameter trends may be used, such as a respiratory rate trend, a respiratory rate variability trend, an RSBI trend, or an RSBI variability trend, among others. The risk generator 236 may determine the WHF risk indicator using a pre-determined mapping f between (1) a WHF risk (R) and (2) a plurality of respiratory parameter trends $(X_1, X_2, \ldots, X_K)$ and the dyspnea descriptor (D), that is, $R=f(X_1, X_2, \ldots, X_K, D)$, where K denotes the number of respiratory parameter trends. In an example, the mapping f may be represented by a look-up table or an association map, where each pre-determined WHF risks, R(i), is associated with (1) the K respiratory parameter trends falling within respective value ranges, denoted by $X_1(i), X_2(i), \ldots, X_K(i)$, and (2) the dyspnea descriptor (D) falling within one of the categories or a range of intensity scores in a rating scale falling within respective value ranges, denoted by D(i). For example, a WHF risk category may be characterized as respiratory rate between 15-25 breaths per minute (bpm), respiratory rate variability (such as determined as a maximum variation within a minute, a day, or other specified time range, $10^{th}$ to $90^{th}$ percentile range within a day, or a standard deviation within a day) between 0-6 bpm, and dyspnea descriptor of "moderate dyspnea" or a dyspnea intensity score of 4-6 in a rating scale.

Additionally or alternatively, the risk generator 236 may determine the WHF risk indicator using a weighted combination of the respiratory parameter trend and the dyspnea descriptor. The dyspnea descriptor 222 may take numerical values according to the rating scale of dyspnea intensity. The respiratory parameter trend may also take numerical value, such as the measured value or normalized value of the respiration parameter. The WHF risk indicator may be determined as a combination of the respiratory parameter trend and the dyspnea descriptor each weighted by their respective weight factors. In an example, the risk generator 236 may generate the WHF risk indicator using a weighted sum of the numerical representations of the respiratory parameter trend and the dyspnea descriptor. The weight factors may be determined using the historical performances of the respiratory parameter trend and the dyspnea descriptor in predicting the patient WHF risk. The weight factors may also be determined using patient population data.

The control circuit 240 may control the operations of the sensor circuit 210, the user interface 220, the risk analyzer circuit 230, and the data and instruction flow between these system components. The control circuit 240 may control the risk generator 236 to generate a WHF risk indicator when one or more of the respiratory parameter trend or the dyspnea satisfy their respective conditions. As illustrated in FIG. 2, the control circuit 240 may include a data acquisition (DAQ) control 242 configured to trigger the acquisition of the dyspnea descriptor 222 using the respiration measurement. The DAQ control 242 may control the input circuit of the user interface 220 to receive the dyspnea descriptor 222 when the respiratory parameter trend satisfies a specific condition. A large respiratory rate, a large RSBI, a large variability or reduced regularity of respiratory rate, or a large variability or reduced regularity of RSBI may each indicate an elevated risk of developing a WHF event. In an example, the input circuit of the user interface 220 may be configured to receive the dyspnea descriptor 222 when one or more of the RRT, the respiratory rate variability trend, the RSBI trend, or the RSBI variability trend exceed their respective thresholds. A questionnaire may be displayed on a user interface to prompt the user for dyspnea symptom input. The dyspnea symptom inquiry may provide additional diagnostic information to the risk generator 236 to assess patient WHF risk. In some examples, the DAQ control 242 may control the input circuit to receive the dyspnea descriptor 222 during a specified time period of daytime or nighttime, or in a specific context such as when the patient is asleep, or when the patient is physically active. In another example, the DAQ control 242 may control the input circuit to receive the dyspnea descriptor 222 periodically at specific times based on patient daily routine, such as when patient is likely physically active, physically inactive, at sleep, or in other specific physical states.

In some examples, the DAQ control 242 may use the dyspnea descriptor to trigger the respiratory data acquisition at the sensor circuit 210, or the trending of the respiration measurement over time at the trending circuit 234. The DAQ control 242 may generate the respiratory parameter trend when the received dyspnea descriptor satisfies a specified condition, such as when the dyspnea becomes symptomatic, corresponding to a categorical dyspnea descriptor of "mild" or above, or a numerical dyspnea score exceeding a score threshold (e.g., dyspnea score of 1).

Triggered dyspnea descriptor acquisition using the respiration measurement, or triggered respiratory data acquisition or respiratory parameter trending using the dyspnea symptom, may be beneficial in a sensor-based HF management system. Activation and operation of multiple sensors (e.g., respiratory sensors) may be power- and memory-demanding. On the other hand, continuous acquisition of dyspnea symptom information can be expensive or otherwise impractical particularly in a setting of ambulatory monitoring. The triggered acquisition of one diagnostic using another diagnostic, as discussed in this document, may reduce the total activation time of the respiratory sensors and dyspnea symptom acquisition, and therefore conserve device power and improve the efficiency of device storage and computing resources. The triggered acquisition may also allow synchronous acquisition of dyspnea symptom information and respiratory measurement. This may accurately capture the patient physiological state at the time of testing. Compared to asynchronously acquired dyspnea information such as symptomatic dyspnea, retrieved from patient medical record, that occurred weeks or months prior, the synchronously acquired dyspnea symptom and objective respiratory measurement may offer better complementary predictive power for assessing patient WHF risk.

The optional therapy circuit 250 may be configured to deliver a therapy to the patient in response to the WHF risk satisfying a condition, such as exceeding the risk threshold. Examples of the therapy may include electrostimulation therapy delivered to the heart, a nerve tissue, other target tissues, a cardioversion therapy, a defibrillation therapy, or drug therapy including delivering drug to a tissue or organ. In some examples, the therapy circuit 250 may modify an existing therapy, such as adjust a stimulation parameter or drug dosage.

Although the discussion herein focuses on WHF risk, this is meant only by way of example but not limitation. Systems, devices, and methods discussed in this document may also be suitable for detecting various sorts of diseases or for assessing risk of developing other worsened conditions, such as cardiac arrhythmias, heart failure decompensation, pulmonary edema, pulmonary condition exacerbation, asthma and pneumonia, myocardial infarction, dilated cardiomyopathy, ischemic cardiomyopathy, valvular disease, renal disease, chronic obstructive pulmonary disease, peripheral vascular disease, cerebrovascular disease, hepatic disease, diabetes, anemia, or depression, among others.

Figure 3:
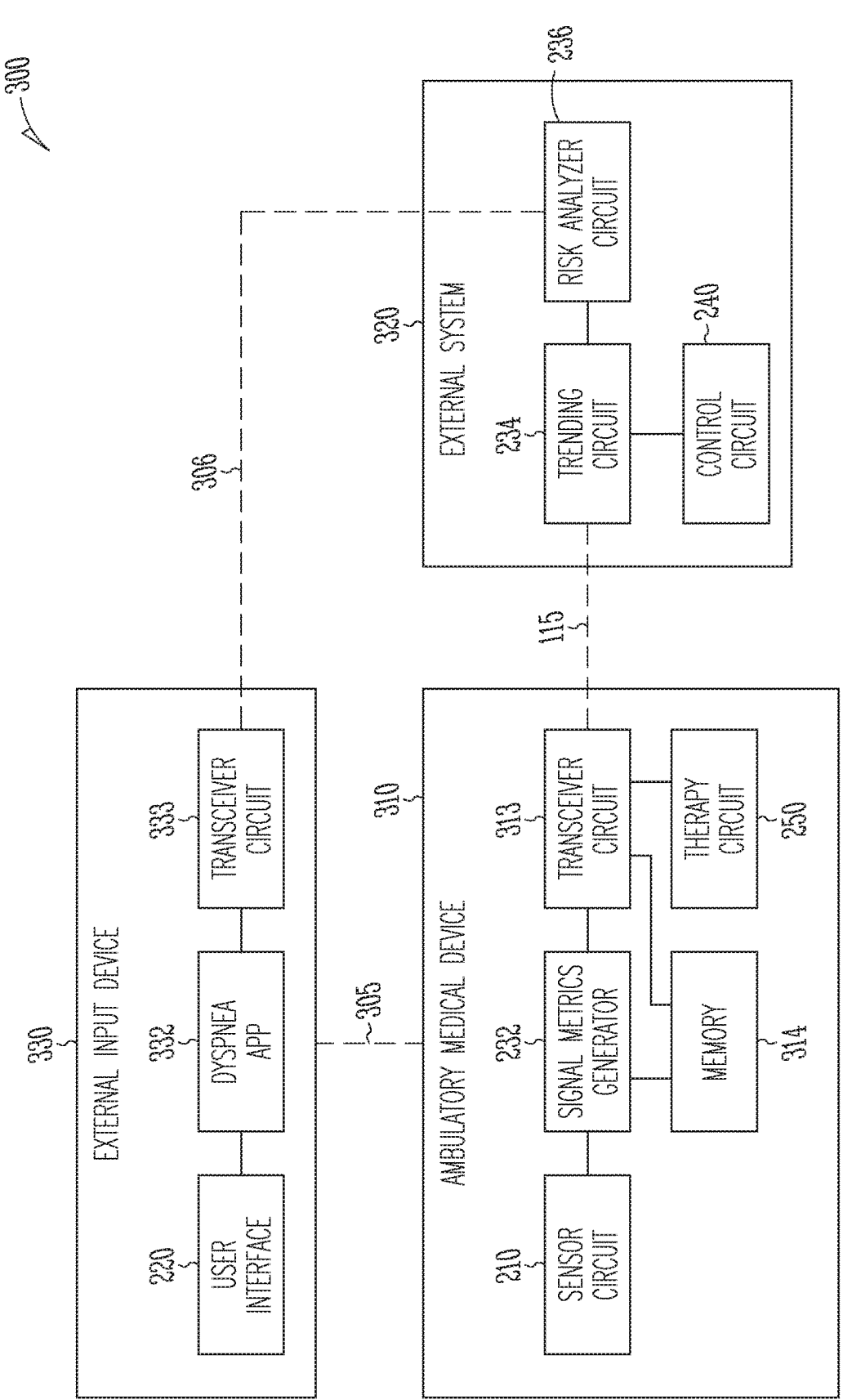
FIG. 3 illustrates generally another example of a HF monitor system configured to assess a risk of WHF.

FIG. 3 illustrates generally another example of a HF monitor system 300 configured to assess a risk of WHF. The HF management system 300, which is an embodiment of the system 100 or the HF monitor system 200, may include an ambulatory medical device (AMD) 310, an external system 320, and an external input device 330. The AMD 310 and the external system 320 may respectively be embodiments of the AMD 110 and the external system 130 as illustrated in FIG. 1. The external system 320 may be communicatively coupled to the AMD 310 via the communication link 115.

The external input device 330 may be a portable device, such as an implantable or wearable patient monitor, a portal electronic device such as a smart phone, a smart wearable, a portable health monitor, a tablet, a laptop computer, or other types of portable computerized device. Alternatively, the external input device 330 may be a stationary device. The external input device 330 may include the user interface 220 configured to receive user input of the dyspnea descriptor 222, as discussed previously with reference to FIG. 2. The user interface 220 may include a display configured to display a dyspnea questionnaire. The user is prompted to answer the questions or act as instructed, such as to input a description of dyspnea intensity, duration, or pattern, using input means such as a keyboard or a touchpad, or to select from a plurality of pre-determined dyspnea descriptors one or more options that best characterize the dyspnea symptom. Additionally or alternatively, the user interface 220 may be coupled to a voice recorder to record patient verbal description of the dyspnea symptoms. In some examples, the user interface 220 may operate in a passive mode by extracting information about dyspnea from patient spontaneous speech, such as when the patient answers a phone call or leaves a voice mail.

The external input device 330, such as a mobile device, may execute mobile applications ("apps") including a dyspnea app 332 configured to process the received dyspnea descriptor 222, such as to categorize patient verbal description of dyspnea symptom into different categories or associate the dyspnea symptom to different dyspnea scores according to a rating scale.

The external input device 330 may include a transceiver circuit 333 configured to transmit the dyspnea symptom information to the AMD 310 via a communication link 305. Examples of the communication link 305 may include a wired connection including universal serial bus (USB) connection, or otherwise cables coupled to communication interfaces on both the mobile device 400 and the AMD 302. Alternatively, the communication link 305 may include a wireless connection including Bluetooth protocol, Ethernet, IEEE 802.11 wireless, an inductive telemetry link, or a radio-frequency telemetry link, among others.

The AMD 310 may include the sensor circuit 210 coupled to a respiratory sensor configured to acquire a respiration measurement, and the signal metrics generator 232 configured to generate one or more metrics from the respiration measurements. The respiration measurement may be acquired continuously or periodically. In an example, the respiration measurement may be acquired when the external input device 330 receives a dyspnea descriptor that satisfies a specific condition, such as a symptomatic dyspnea with a categorical value of "mild" or above, or a numerical dyspnea score exceeding a score threshold (e.g., dyspnea score of 1). In some examples, the respiration measurement may be acquired in a command mode. The external input device 330 may include a user control, in the form of a button or an on-screen control or other control means, that enables a user to issue a command to activate respiration measurement acquisition at the AMD 310, or to control the trending of respiration measurement and risk analysis at the external system 320.

The respiration measurements or respiratory metrics may be stored in a memory 314. Data storage at the memory 314 may be continuous, periodic, or triggered by a user command or a specified event. The AMD 310 may include a transceiver circuit 313 that may receive from the external input device 330 the information about dyspnea symptoms, or a user command to activate respiratory data acquisition. The information about dyspnea symptoms may also be stored in the memory 314. The AMD 310 may include the therapy circuit 250 configured to generate and deliver electrostimulation energy according to specified stimulation parameters, or via specified electrodes. The stimulation parameters and stimulation electrode configuration may be provided by a system user, such as a clinician. The AMD 310 may receive the information about electrostimulation parameters and the electrode configuration from the external system 320 via the communication link 115.

The external system 320, which is an embodiment of the external device 115, or the remote device 124, may include one or more of the trending circuit 234, the risk analyzer circuit 236, and the control circuit 240. Respiratory signal metrics generated at the AMD 310 may be forwarded to the external system 310 via the communication link 115. The trending circuit 234 may generate one or more respiratory parameter trends, such as a respiratory rate trend, a respiratory rate variability trend, a RSBI trend, or a RSBI variability trend. The dyspnea symptom information, which is stored in the memory 314 of the AMD 310, may also be transmitted to the external system 320. The risk analyzer circuit 236 may generate the WHF risk using the dyspnea symptom information and one or more respiratory parameter trends, as discussed previously with reference to FIG. 2.

The control circuit 240 may control the dyspnea symptom acquisition at the external input device 330, the respiratory data acquisition at the AMD 310, and the data communication between the AMD 310 and the external system 320. In some examples, the external input device 330 may be communicatively coupled to the external system 320 via the communication link 306. The transceiver circuit 333 may transmit the dyspnea symptom information directly to the external system 320 via the communication link 306 for assessing the WHF risk. The control circuit 240 may control the data communication between the external input device 330 and the external system 320. The communication link 306 may be an inductive telemetry link, a capacitive telemetry link, an RF telemetry link, or wireless telemetry based on, for example, "strong" Bluetooth or IEEE 802.11 wireless fidelity "WiFi" interfacing standards. Other configurations and combinations of patient data source interfacing are possible. The control circuit 240 may include a therapy control circuit that may program the therapy circuit 250, via the communication link 115, to deliver therapy according to the electrostimulation parameters and the electrode configuration.

In an example, in response to the respiratory parameter trend generated to the trending circuit 234 satisfying a specific condition, the control circuit 240 may send a dyspnea inquiry command to the external input device 330, either directly via the communication link 306, or indirectly via the AMD 110. The external input device 330 may display a questionnaire on the user interface 220, or otherwise generate a perceptible signal prompting the user to input dyspnea descriptor using the user interface 220. Additionally or alternatively, in response to a user input of symptomatic dyspnea or when the dyspnea descriptor satisfies a specified condition (e.g., falls into a dyspnea category or exceeds a dyspnea rating threshold), the control circuit 240 may send a respiratory data acquisition command to the AMD 310 to trigger the respiratory data acquisition, or to activate respiration parameter trending at the trending circuit 234. In some examples, at least a part of the control circuit 240 may be implemented in the AMD 310, and the control circuit 240 may control the dyspnea symptom acquisition using the respiratory parameter trend, or control the respiratory data acquisition in response to the dyspnea descriptor transmitted through the communication link 305.

Figure 4:
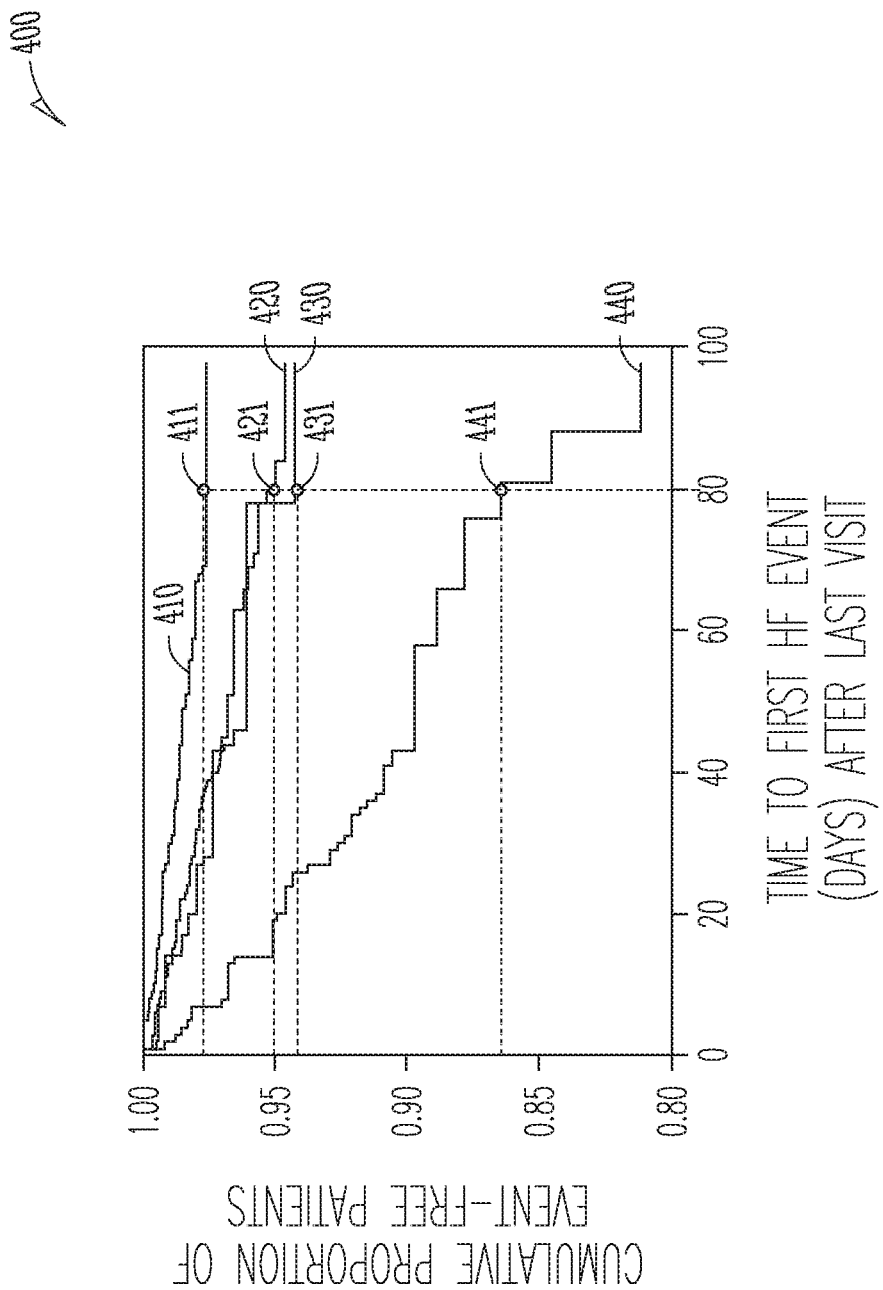
FIG. 4 illustrates generally a graph showing statistical analysis of WHF risks in patients having one or both of dyspnea symptom and sensor-indicated respiratory changes.

FIG. 4 illustrates generally a graph 400 showing statistical analysis of WHF risk in patients having one or both of dyspnea symptom and sensor-indicated respiratory changes. The graph 400, which is known as Kaplan-Meier plot, represents a cumulative proportion (e.g., a percentage) of patients, in a particular patient cohort, that are free of WHF event (shown in vertical axis) at various observation times (shown in horizontal axis) from patient last clinic visit to patient first WHF event such as a HF decompensation event. By way of example and not limitation, four curves are plotted in the graph 400. Curve 410 represents a WHF risk curve obtained from a first patient cohort free of dyspnea symptoms and having a respiratory rate trend (RRT) falling below a respiration threshold ($RRT_{TH}$). In an example, the $RRT_{TH}$ is approximately 20 breaths per minute (bpm). Curve 420 represents a WHF risk curve obtained from a second patient cohort presenting with symptomatic dyspnea, but no substantial respiratory abnormality, with RRT less than $RRT_{TH}$. Curve 430 represents a WHF risk curve obtained from a third patient cohort free of symptomatic dyspnea, but having an elevated respiratory rate with RRT>$RRT_{TH}$. Curve 440 represents a WHF risk curve obtained from a fourth patient cohort presenting with symptomatic dyspnea, and having an elevated respiratory rate with RRT>$RRT_{TH}$.

As illustrated in FIG. 4, the WHF risk curves 410-440 demonstrate distinct patterns over time during a period of approximately 100 days from patient last clinic visit and prior to patient first WHF event (e.g., a HF decompensation event or HF hospitalization). For example, the first patient cohort (corresponding to the curve 410) generally maintains highest WHF event-free patient fraction among the four patient cohorts during the observation period. The second and third patient cohorts (corresponding to the curves 420 and 430, respectively) each demonstrates lower WHF event-free patient fraction than the first patient cohort does. For example, at 80-day mark after last clinic visit and prior to the first WHF event, about 98% of the patients in the first cohort do not experience the WHF event post last clinic visit, as indicated by point 411 on the curve 410. At this observation time, only about 95% of the second patient cohort and about 94% of the third patient cohort remain WHF event-free, as indicated by point 421 on the curve 420 and point 431 on the curve 430. The fourth patient cohort (corresponding to the curve 440) has the lowest WHF event-free patient fraction among the four patient cohorts. The difference from other patient cohorts becomes larger as time goes by during the observation period. For example, as indicated by point 441 on the curve 440, at 80-day mark after last clinic visit and prior to the first WHF event, only about 86% of those in the first patient cohort do not experience the first WHF event post last clinic visit.

A comparison of the curves 420 and 430 to the curve 410 suggests that the dyspnea symptoms and the respiratory rate trend each can predict patient WHF risk. A comparison of the curves 420 and 430 to the curve 440 suggests that the dyspnea symptom and the respiratory rate trend may provide orthogonal, or non-redundant, predictive power in identifying patient WHF risk. Information about patient dyspnea symptom may complement the sensor-indicated respiratory abnormality in WHF risk stratification. In particular, patients having both the respiratory abnormality (e.g., elevated RRT exceeding the $RRT_{TH}$) and symptomatic dyspnea have a greater risk of experiencing future WHF than patients with the respiratory abnormality but free of dyspnea symptom, or presented with only symptomatic dyspnea but having a normal respiration measurement (e.g., RRT below the $RRT_{TH}$). The risk generator 236 may determine the WHF risk using the RRT and presence/absence of patient dyspnea symptoms. One or more respiratory parameters may be used in addition to or in lieu of the RRT. The respiratory parameters and/or the dyspnea symptoms may each be classified into respective multiple categories, and the risk generator 236 may categorize the WHF risk using the classified respiratory parameters and/or the classified dyspnea symptom.

Figure 5:
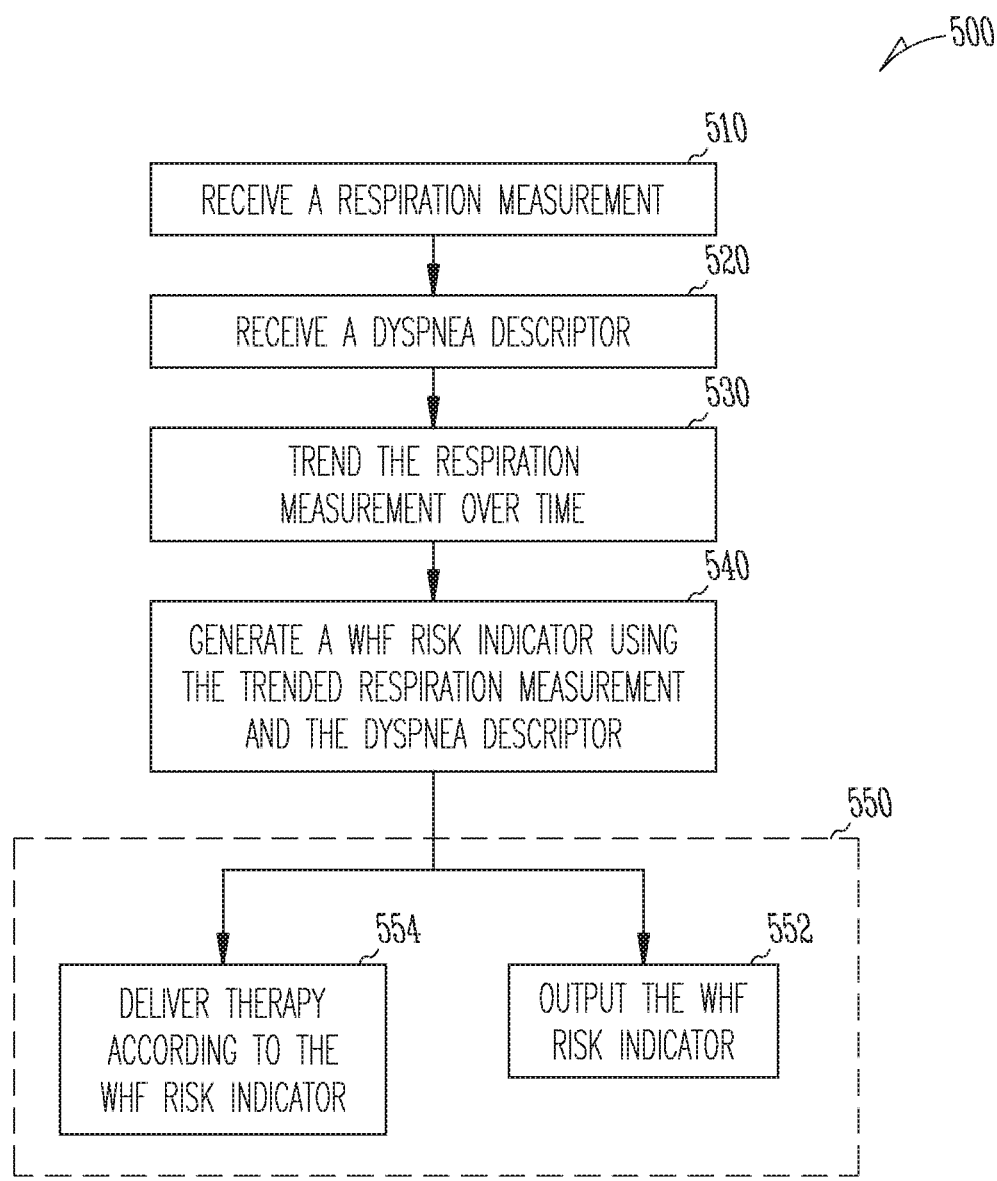
FIG. 5 illustrates generally an example of a method for monitoring heart failure to assess a patient WHF risk.

FIG. 5 illustrates generally an example of a method 500 for monitoring heart failure (HF) to assess a patient WHF risk. The method 500 may be implemented and executed in an ambulatory medical device (AMD) such as an implantable or wearable medical device, or in a remote patient management system. In various examples, the method 500 may be implemented in and executed by the AMD 110, one or more devices in the external system 125, or the HF monitor system 200 or a modification thereof.

The method 500 begins at 510, where a respiration measurement may be received. In an example, the respiration measurement may be sensed and acquired using the sensor circuit 210 that is coupled to one or more physiological sensors. A respiratory signal may be sensed using various physiological sensors, as previously discussed with reference to FIG. 2. The sensed respiratory signal may include a respiration waveform that represents the change in airflow or lung volume during a respiratory cycle. Alternatively, the sensed physiological signal, such as a thoracic impedance signal or a cardiac electrical activity signal, may be modulated by respiration, and can be demodulated to obtain the respiratory signal such as by using one or more signal filters. In some examples, the respiratory signal sensed from a patient may be stored in a storage device, such as an electronic medical record (EMR) system. The respiration measurement may be retrieved from the storage device in response to a user input or triggered by a specific event.

At 520, a dyspnea descriptor indicating a severity of patient symptomatic dyspnea may be received via the user interface 220 or from the external device 330 such as a mobile device, as discussed previously with reference to FIGS. 2-3. Symptomatic dyspnea may be indicative of WHF. The dyspnea descriptor may include information about intensity, duration, or pattern of the dyspnea symptoms. The dyspnea descriptor may take different forms including, by way of example and not limitation, verbal description, written description, categorical values, or numerical values. In an example, a patient questionnaire may be displayed on a user interface, such as of a mobile device. The patient, or other users such as a healthcare professional, may be prompted to enter information about patient dyspnea symptoms, including one or more of dyspnea intensity, duration, pattern, or other symptom descriptors. The user may alternatively be prompted to select from a plurality of prepared dyspnea descriptors.

In some examples, at 520, the dyspnea descriptor may be acquired during a specified time period of daytime or nighttime, or in a specific context such as when the patient is asleep, or when the patient is physically active. Alternatively or additionally, the dyspnea descriptor may be acquired periodically at a specific time, such as a particular time of day when patient is likely to be in a specific physical state according to patient daily routine, such as being physically active, or at sleep or being physically inactive.

At 530, the respiration measurement may be trended over time, such as via the trending circuit 234. In some examples, one or more respiratory metrics may be generated from the respiration measurements, such as one or more of a tidal volume, a respiratory rate, a minute ventilation, a respiratory sound, a rapid-shallow breathing index (RSBI) computed as a ratio of a respiratory rate measurement to a tidal volume measurement, or a respiratory pattern. One or more respiratory metrics may be trended to generate the respiratory parameter trends including, for example, a respiratory rate trend (RRT), a RSBI trend, a respiratory rate variability trend, or a RSBI variability trend.

In various examples, respiration measurements at 510, and the dyspnea descriptor acquisition at 520 and trending of respiratory parameters at 530, may be activated in a triggered mode, such as controlled by the control circuit 240. In an example, the dyspnea descriptor may be acquired at 520 in response to the respiratory parameter trend satisfying a specific condition, such as when the RRT or RSBI exceeds their respective thresholds. In another example, the dyspnea descriptor may be used to trigger the respiratory data acquisition at 510, or the trending of the respiration measurement over time at 530. For example, the respiratory parameter trend may be generated at 530 in response to the received dyspnea descriptor at 520 indicating that the dyspnea becomes symptomatic, having a categorical value of "mild" or above, or having a numerical dyspnea score exceeding a score threshold.

At 540, a WHF risk indicator may be generated using both the respiration measurement and the received dyspnea descriptor, such as via the risk analyzer circuit 230. Information about patient symptomatic dyspnea may provide additional predicative power other than the sensor-indicated respiratory changes. Combining the symptomatic dyspnea information with the respiration measurements may improve sensitivity, specificity, or positive predictive value of WHF detection or WHF risk stratification. As illustrated in FIG. 4, information about the dyspnea symptom and the respiratory rate trend each independently predicts patient WHF risk. Information about patient dyspnea symptom may complement the sensor-indicated respiratory abnormality in WHF risk stratification. Patients with both the respiratory abnormality and symptomatic dyspnea are at substantially greater risk of WHF than patients presented with respiratory abnormality but free of dyspnea symptom, or patients presented with symptomatic dyspnea but having a normal respiration measurement.

In an example, a computation model may be used to compute a linear or nonlinear combination of the respiratory parameter trend and the dyspnea descriptor at 540.

Examples of the computation models may include a weighted combination, a decision tree, a neural network, a fuzzy-logic model, or a multivariate regression model, among others. The WHF risk indicator may be determined using a logic combination of respiratory parameter trend and the dyspnea descriptor. The patient may be designated with a high WHF risk if the respiratory parameter trend exceeds a respiration threshold and the received dyspnea descriptor indicates a presence of dyspnea; a medium WHF risk may be determined if the respiratory parameter trend exceeds the respiration threshold and the patient does not have symptom of dyspnea, or if the respiratory parameter trend falls below the threshold and the patient has symptomatic dyspnea. A low WHF risk may be designated to a patient if the respiratory parameter trend falls below the respiration threshold and the received dyspnea descriptor indicates no symptom of dyspnea.

In another example, the WHF risk indicator may be generated by comparing to a plurality of pre-determined WHF risk categories. Each WHF risk category is characterized by a number of respiratory parameter trends each falling within respective value ranges, and the dyspnea descriptor falling within one of the categories or numerical value ranges.

In yet another example, the WHF risk indicator may be generated using a weighted combination of the respiratory parameter trend and the dyspnea descriptor. The dyspnea descriptor may take numerical values such as according to rating scale of dyspnea symptom intensity. The respiratory parameter trend may also take numerical value, such as the measured value or normalized value of the respiration parameter. The WHF risk indicator may be determined as a combination of the respiratory parameter trend and the dyspnea descriptor each weighted by their respective weight factors. The weight factors may be determined according to respective historical performances of the respiratory parameter trend and the dyspnea descriptor respective in predicting WHF events, or using patient population data.

At 550, the WHF risk indicator may be output to a user or a process. At 552, a human-perceptible presentation of the WHF risk indicator may be generated, and displayed such as on the user interface 220. The information may be presented in a table, a chart, a diagram, or any other types of textual, tabular, or graphical presentation formats. Hard copies of signals and information related to the generation of WHF risk indicator. In an example, alerts, alarms, emergency calls, or other forms of warnings to signal the system user about the WHF detection or risk may be generated. The WHF detection or the WHF risk may be output to a process such as an instance of a computer program executable in a microprocessor.

At 554, the detected WHF risk may trigger a therapy delivered to the patient, such as using the therapy circuit 250. The therapy may be delivered to the patient in response to the WHF risk satisfying a condition, such as exceeding the risk threshold. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy may be modified, such as by adjusting a stimulation parameter or drug dosage.

Figure 6:
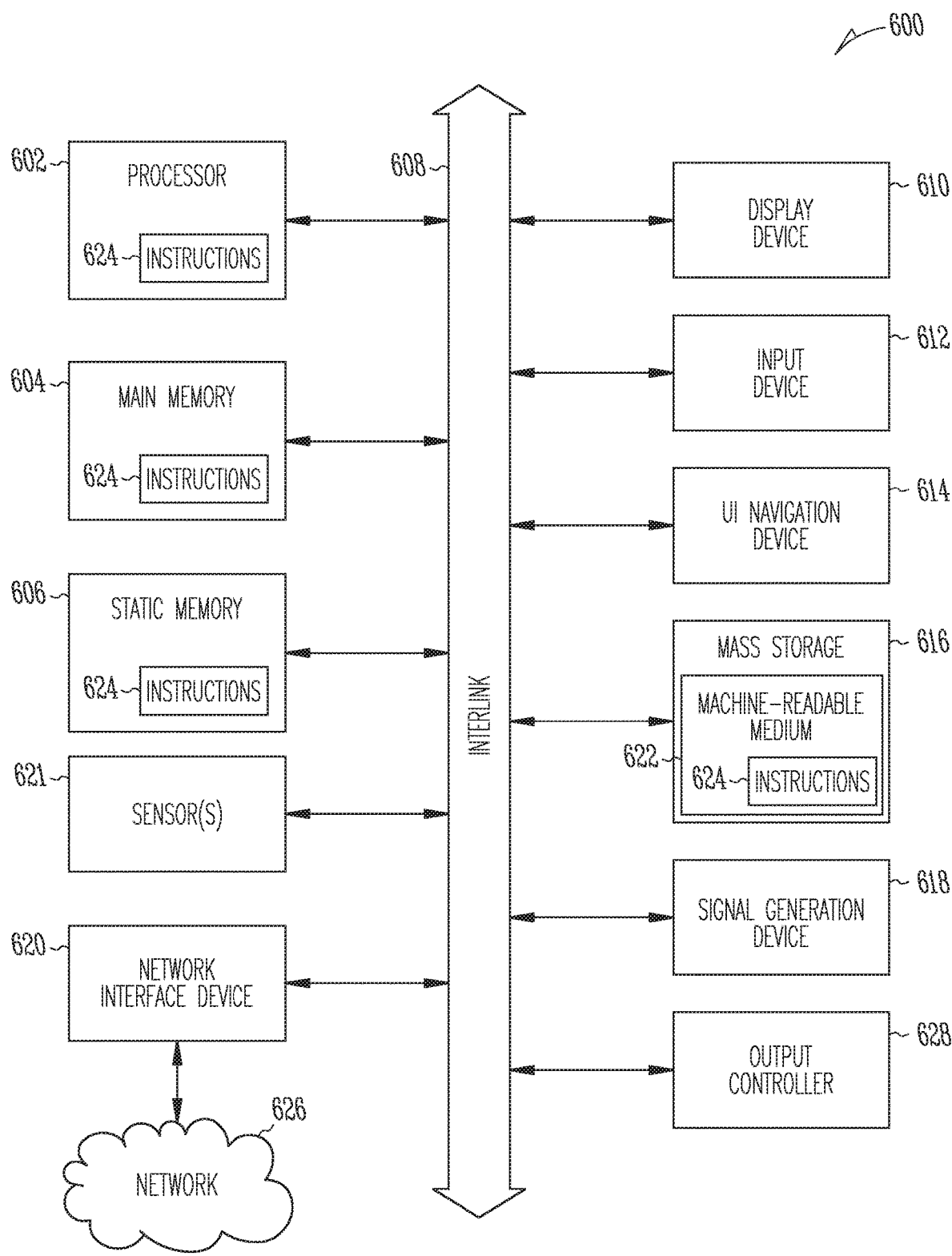
FIG. 6 illustrates generally a block diagram of an example machine upon which any one or more of the techniques discussed herein may perform.

FIG. 6 illustrates generally a block diagram of an example machine 600 upon which any one or more of the techniques (e.g., methodologies) discussed herein may perform. Portions of this description may apply to the computing framework of various portions of the LCP device, the IMD, or the external programmer.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specific operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine-readable media.

While the machine-readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for identifying a worsening heart failure (WHF) risk of a patient, comprising:
    a risk analyzer circuit configured to:
        monitor a respiratory rate of the patient and generate a respiratory rate trend;
        upon the respiratory rate exceeding a respiratory rate threshold, receive a user input of a dyspnea descriptor indicating a dyspnea symptom severity of the patient; and
        generate a WHF risk indicator using the respiratory rate trend and the user input of dyspnea descriptor, including:
            (i) a high WHF risk indicator if the respiratory rate trend is above the respiratory rate threshold and the received dyspnea descriptor indicates a presence of dyspnea;
            (ii) a medium WHF risk indicator if the respiratory rate trend is above the respiratory rate threshold without a presence of dyspnea, or the respiratory rate trend falls below the respiratory rate threshold and the received dyspnea descriptor indicates a presence of dyspnea; and
            (iii) a low WHF risk indicator if the respiratory rate trend is below the respiratory rate threshold; and
    an output circuit configured to generate a real-time alert in response to generating the high WHF risk indicator or the medium WHF risk indicator.

2. The system of claim 1, further comprising a respiration sensor circuit configured to sense from the patient a respiratory signal and to determine the respiratory rate from the sensed respiratory signal.

3. The system of claim 1, wherein the risk analyzer circuit is configured to further generate a respiratory rate variability trend, and to generate the WHF risk indicator further using the respiratory rate variability trend.

4. The system of claim 1, wherein the risk analyzer circuit is configured to further generate a rapid-shallow breathing index (RSBI) trend or a RSBI variability trend, and to generate the WHF risk indicator further using the RSBI trend or the RSBI variability trend.

5. The system of claim 1, further comprising an external device configured to receive the user input of the dyspnea descriptor.

6. The system of claim 5, wherein the external device includes a mobile device communicatively coupled to the risk analyzer circuit, the mobile device configured to prompt a user to input the dyspnea descriptor in response to the respiratory rate trend-being above the respiratory rate threshold.

7. The system of claim 5, wherein the external device is configured to receive a user trigger to activate the risk analyzer circuit to trend the respiratory rate and to generate the WHF risk indicator.

8. The system of claim 1, wherein the dyspnea descriptor includes a rating of dyspnea symptom severity on a specific rating scale, and the risk analyzer circuit is configured to generate the WHF risk indicator using a combination of the rating of dyspnea symptom severity and the respiratory rate trend each weighted by respective weight factors.

9. The system of claim 1, wherein the output circuit is configured to generate a recommendation for initiating or adjusting a therapy for the patient.

10. The system of claim 1, wherein the receiver circuit is configured to receive the user input of the dyspnea descriptor in response to the respiratory rate trend being above a threshold.

11. The system of claim 1, wherein the receiver circuit is further configured to receive the user input of the dyspnea descriptor during a specified time period of a day or when the patient is in a specific state.

12. The system of claim 1, further comprising a therapy circuit configured to initiate or adjust a heart failure therapy in response to generating the high WHF risk indicator or the medium WHF risk indicator.

13. A system, comprising:
an ambulatory medical device (AMD) including a sensor circuit configured to sense a respiratory signal and to determine a respiratory parameter including a respiratory rate from the sensed respiratory signal;
a mobile device configured to receive a user input of a dyspnea descriptor indicating a severity of dyspnea symptom upon the respiratory rate exceeding a threshold;
an external device communicatively coupled to the AMD and the mobile device, the external device configured to:
generate a respiratory rate trend;
generate a worsening heart failure (WHF) risk indicator using the respiratory rate trend and the user input of dyspnea descriptor, including:
(i) a high WHF risk indicator if the respiratory rate trend is above the respiratory rate threshold and the received dyspnea descriptor indicates a presence of dyspnea;
(ii) a medium WHF risk indicator if the respiratory rate trend is above the respiratory rate threshold without a presence of dyspnea, or the respiratory rate trend is below the respiratory rate and the received dyspnea descriptor indicates a presence of dyspnea; and
(iii) a low WHF risk indicator if the respiratory rate trend is below the respiratory rate threshold; and
generate a real-time alert in response to generating the high WHF risk indicator or the medium WHF risk indicator.

14. A method for identifying a worsening heart failure (WHF) risk of a patient via a medical system, comprising:
monitoring a respiratory rate of the patient via a risk analyzer circuit;
generating a respiratory rate trend via the risk analyzer circuit;
upon the respiratory rate exceeding a respiratory rate threshold, receiving a user input of a dyspnea descriptor indicating a dyspnea symptom severity of the patient;
generating, via the risk analyzer circuit, a WHF risk indicator using the respiratory rate trend and the user input of dyspnea descriptor, including:
(i) a high WHF risk indicator if the respiratory rate trend is above the respiratory rate threshold and the received dyspnea descriptor indicates a presence of dyspnea;
(ii) a medium WHF risk indicator if the respiratory rate trend is above the respiratory rate threshold without a presence of dyspnea, or the respiratory rate trend falls below the respiratory rate and the received dyspnea descriptor indicates a presence of dyspnea; and
(iii) a low WHF risk indicator if the respiratory rate trend is below the respiratory rate threshold; and
generating a real-time alert in response to generating the high WHF risk indicator or the medium WHF risk indicator.

15. The method of claim 14, further comprising generating a prompt on an external device for a user input of the dyspnea descriptor in response to the respiratory rate trend being above the respiratory rate threshold.

16. The method of claim 14, further comprising generating a trend of at least one of:
a respiratory rate variability;
a rapid-shallow breathing index (RSBI); or
a RSB variability;
wherein generating the WHF risk indicator further includes using at least one of the respiratory rate variability trend, the RSBI trend, or the RSBI variability trend.

17. The method of claim 14, wherein the dyspnea descriptor includes a rating of dyspnea symptom severity on a specific rating scale, and wherein generating the WHF risk indicator includes using a combination of the rating of dyspnea symptom severity and the respiratory rate trend each weighted by respective weight factors.

18. The method of claim 14, wherein receiving the user input of the dyspnea descriptor is in response to the respiratory rate trend being above a threshold.

19. The method of claim 14, wherein receiving the user input of the dyspnea descriptor occurs further during a specified time period of a day or when the patient is in a specific state.

20. The method of claim 14, further comprising generating a recommendation for initiating or adjusting a therapy for the patient based on the WHF risk indicator.

* * * * *